United States Patent [19]

Waxman et al.

[11] Patent Number: 4,567,035

[45] Date of Patent: Jan. 28, 1986

[54] LOW MOLECULAR WEIGHT HAIR SPRAY

[75] Inventors: Burton H. Waxman, Rockaway; I. Sioun Lin, Oak Ridge, both of N.J.

[73] Assignee: GAF Corporation, Wayne, N.J.

[21] Appl. No.: 525,357

[22] Filed: Aug. 22, 1983

[51] Int. Cl.$^4$ .......................... A61K 7/11; A61K 31/74
[52] U.S. Cl. ................................ 424/47; 424/DIG. 1; 424/2; 424/4; 424/70; 424/78
[58] Field of Search ...................... 424/DIG. 1, 70, 47, 424/78, DIG. 2, DIG. 4; 525/327.7

[56] References Cited

U.S. PATENT DOCUMENTS

| | | | |
|---|---|---|---|
| 2,360,071 | 11/1947 | McNally et al. | 525/327.7 |
| 2,454,284 | 11/1948 | Kirk | 525/327.7 |
| 2,913,437 | 11/1959 | Johnson | 424/DIG. 1 |
| 3,212,972 | 10/1965 | Bailey, Jr. | 424/DIG. 1 |
| 3,285,819 | 11/1966 | Blance et al. | 424/DIG. 1 |
| 3,530,101 | 9/1970 | Haynes et al. | 525/327.7 |
| 3,922,341 | 11/1975 | Abegg et al. | 424/DIG. 1 |
| 4,164,562 | 8/1979 | Nandagiri | 424/DIG. 1 |

FOREIGN PATENT DOCUMENTS

| | | | |
|---|---|---|---|
| 631883 | 11/1961 | Canada | 424/327.7 |
| 950766 | 2/1964 | United Kingdom | 525/327.7 |

OTHER PUBLICATIONS

Root, Cosmetics & Toiletries, 3/1979, vol. 94, pp. 37, 38 & 40.

Root (II), Drug and Cosmetic Industry, 3/1965, vol. 96, No. 3, pp. 327, 328, 416, 417, 422 and 423.

*Primary Examiner*—Dale R. Ore
*Attorney, Agent, or Firm*—Marilyn J. Maue; Joshua J. Ward

[57] ABSTRACT

A low molecular weight hair spray resin containing a vinyl monomer having a

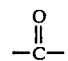

electron withdrawing group and consisting essentially of alternating units of vinyl ester and an alkyl half ester maleate derived from an alternating vinyl ester/maleic anhydride copolymer. The resins of this invention are defined by the structure:

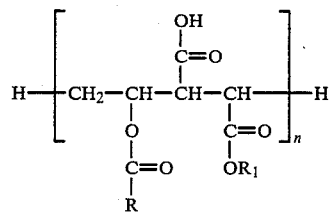

wherein R and $R_1$ are each independently alkyl having from 1 to 6 carbon atoms and n has a value between about 40 and 250, preferably 60 to 220.

9 Claims, No Drawings

LOW MOLECULAR WEIGHT HAIR SPRAY

This invention relates to the preparation of low molecular weight resins especially suitable for use in aerosol and pump formulations, and more particularly, to film forming polymeric substances employed for hair sprays and having excellent hair holding capability at high humidity.

In order to be highly effective in hair spray formulations, film forming polymeric components utilized therein as well as the films they deposit must meet a rigid set of requirements. Thus, the resulting films should maintain their non-tacky state under conditions of high humidity; they should be easily removable in aqueous soap solutions or shampoos; and they should have a viscosity range which permits uniform spraying without clogging of the spray nozzle. Additionally the films should be cohesive and yet have sufficient strength and elasticity; they should adhere well to hair so as to avoid dusting or flaking off when the hair is subjected to varying stresses; they should readily allow the hair to be recombed; they should be clear, transparent and glossy and should maintain this clarity on aging; they should be readily soluble in the solvents which are commonly used in hair spray formulations and miscible with aerosol propellants; and they should show little or no tendency to interact with the perfumes or other optional components conventionally utilized in hair spray lacquer formulations. Finally, they should avoid the initiation of spray can corrosion; and preferably, should be capable of being produced in an efficient and economical manner.

Needless to say, many polymeric systems have been utilized in an attempt to meet these stringent requirements. Among these are included: polyvinylpyrrolidone and copolymers of N-vinyl pyrrolidone with vinyl acetate. However, these copolymers do not exhibit the desired degree of holding at high humidity. Moreover, several of the pyrrolidone polymers possess an unpleasant odor. Vinyl ether/maleic half esters have also been used in hair sprays, but these copolymers require high molecular weight in order to provide adequate holding. Additionally vinyl acetate polymers having 15 to 35 percent of their acetate groups converted to hydroxyl groups have been proposed for increasing solubility in carbon dioxide propellant systems. However, such increased solubility is achieved at the cost of lowered holding power. Although each of the above resins meets at least some of the above cited requirements, none has exhibited all of these characteristics to a desired degree.

Accordingly, it is an object of the present invention to overcome the individual deficiencies of the above discussed copolymers and to provide an improved half acid/half ester, alcohol soluble resin ideally suited for hair sprays.

It is another object of this invention to provide a convenient and economically produced copolymer of low molecular weight for use in spraying applications.

Still another object of this invention is to provide a low molecular weight vinyl ester/maleic anhydride half ester resin having an alternating structure for use in hair sprays and having excellent hair holding capability even under conditions of high humidity.

Another object is to provide a low molecular weight vinyl ester/maleic anhydride half ester resin which obviates spray can corrosion.

Another object is to provide a low molecular weight vinyl ester/maleic anhydride half ester resin having a superior low cloud/clear temperature point.

These and other objects will become apparent from the following description and disclosure.

According to this invention there is provided a hair spray resin copolymer of a linear or branched chain vinyl monomer having a

electron withdrawing group and an alkyl half ester of a maleic acid having essentially an alternating structure and derived from an alternating vinyl ester/maleic anhydride copolymer. The hair spray resins of the present invention are identified by the formula

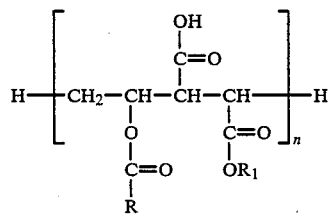

wherein R and $R_1$ are each independently an alkyl group having from 1 to 6 carbon atoms and n has a value of between about 40 and 250, preferably between about 60 and about 220. The relative viscosity, 1% solid in SDA*-40-2 anhydrous alcohol, of the present resins is within the range of from about 1.12 to about 2.03 preferably from 1.15 to 1.54.

*denatured alcohol

Of the present hair spray resins, those wherein R is methyl, ethyl or propyl and $R_1$ is ethyl, isopropyl or butyl or mixtures thereof, are most preferred.

To obtain the vinyl ester/half ester maleate copolymers of this invention, it is essential to prepare the copolymer from a preformed vinyl ester/maleic anhydride copolymer having an alternating structure. The preparation of such alternating vinyl ester-maleic anhydride copolymers is described in *Journal of Polymer Science*, Vol. V, No. 2, pages 253–258, 1950.

To arrive at the present resins, the preformed alternating vinyl ester-maleic anhydride copolymer is subjected to esterification with an organic alcohol containing the number of carbon atoms corresponding to $R_1$ above. Only in this way is the alternating structure of the individual monomers obtained. Polymerizations of vinyl ester with an alkyl maleate produces random or block polymers wherein the faster reacting alkyl maleate monomer forms homopolymer segments with relatively small numbers of polyvinyl ester interposed between or terminating an alkyl maleate chain. These block polymers lack uniform hair holding capability and are not sufficiently hair substantive so that there is a tendency to leave flaky deposits on the hair after drying. The present polymers have the same hair holding capability as GANTREZ ®, a copolymer of a vinyl ether and an alkyl maleate, and also possess equivalent high humidity resistance; but most advantageously, the present polymers provide these properties in the form of resins having significantly lower molecular weights as indicated by the low relative viscosities and K values found for the present copolymers. The K values range from about 20 to about 60, preferably from about 24 to about 45. The lower molecular weight resins enable improvement in the ease of handling in that they remain highly fluid concentrates at low temperature and are readily pumpable from storage containers. Also, they allow for the preparation of concentrates having a significantly higher solids content. When incorporated into a hair spray formulation, these low viscosity polymers are atomized through a spray nozzle without clogging and thus provide more uniform coverage of the hair. The excellent hair holding capability and low molecular weight in a hair spray resin is a most unusual combination of properties, since generally the molecular weight of the polymer and its hair holding capability are directly proportional. As shown in the following examples, the present alternating vinyl ester/alkyl maleate copolymers have superior hair holding properties to other maleate resins of equivalent relative viscosity.

An important difference between GANTREZ® and the present resin resides in the electron withdrawing

group of the vinyl ester moiety, as opposed to the —O— electron donating moiety of the vinyl ether copolymers. However, the presence of any electron withdrawing group in the absence of the ester moiety, as for example the carbonyl radical in the vinyl pyrrolidone monomer of the vinyl pyrrolidone/ethyl maleate or vinyl acetate copolymers, does not provide the advantages of the present invention as illustrated in the following examples. The copolymers of the present type require no neutralization to increase their water solubility for ease of removal from the hair during washing; whereas the vinyl ether copolymer requires neutralizer or solubilizer to achieve shampooability.

The present resins are significantly superior to the vinylpyrrolidone/vinyl acetate or maleate copolymers since the later have shown deficiency in high humidity hair holding tests. Other advantages include substantially lower cloud and clear points and excellent non-corrosive properties. In view of the significantly inferior high humidity hair holding properties of such polymers as vinyl pyrrolidone/vinyl acetate, vinyl pyrrolidone/vinyl maleate, hydrolyzed polyvinyl acetate and the tendency of the higher molecular weight vinyl ether/alkyl maleate resins to develop tack under humid conditions, the excellent high humidity hair holding capability and non-tackiness of the present copolymers is surprising.

The elasticity of the present copolymers is attributable to the alternating distribution of vinyl ester/maleic anhydride half ester units, which structure is difficult to achieve since the reactivity of the monomers is widely divergent. Because the reaction rate for maleic half esters is more rapid than that of the vinyl ester, block polymers, random polymers or vinyl ester terminated homopolymers of maleic anhydride ester are more easily obtained. Obviously these copolymers do not possess the necessary alternating structure containing uniform distribution of the hair substantive monomer, i.e. the vinyl ester, and the monomer contributing high film strength i.e. the maleate. The present resins having alternating monomer structure and containing an approximate 50/50 mole ratio of vinyl ester/maleic anhydride half ester units, is also an important factor in providing the soap solution solubility of the hair spray resin. Accordingly, it is essential that the present resins be derived from a preformed vinyl ester/maleic anhydride alternating copolymer under specific reaction conditions for subsequent esterification of the anhydride moiety.

According to this invention, the resins employed herein are prepared by a two-step process involving, as the first step, the anhydrous polymerization of maleic anhydride and a vinyl ester, ideally in stoichiometric amounts, in the presence of an aromatic solvent such as toluene, benzene, xylene, and the like or any other inert organic liquid, such as acetone, methylene chloride, pentane, hexane, heptane, etc. The total monomer concentration in the solvent must be maintained between about 10% and about 75% by weight, preferably in the range of 20% to 50% by weight to achieve lower molecular weight polymers of this invention. Broadly the mole ratio of vinyl ester to maleic anhydride can be between about 0.8:1 and about 1.3:1. However, a slight molar excess of the vinyl ester, eg. up to about 1.1 is preferred.

The polymerization is necessarily carried out in a nitrogen or anhydrous atmosphere at a low temperature not in excess of 93° C. and preferably within the range of from about 40° C. to about 85° C. at from about 0 to about 100 psi. Above 93° C. the charge transfer complex of the monomers, which provides for the desired alternating structure of the copolymer, does not exist and random copolymers are formed. These random copolymers do not provide suitable hair spray resins having the advantages set forth in the present invention.

The polymerization is also effected in the presence of a catalyst having chain initiating properties. Examples of such catalysts include 2,2'-azobis(2,4-dimethylvaleronitrile), azobis(isobutyronitrile), tert-butylperoxy pivalate, potassium or sodium persulfate, etc. It is important that the catalyst concentration in the reaction mixture be maintained to yield a resin within the desired molecular weight range. A preferred molecular weight range is achieved with resins possessing a relative viscosity of between about 1.15 and about 1.54. Resins having a relative viscosity below 1.12 generally lack sufficient hair holding capability, while resins having a relative viscosity above 2.03 generally exhibit poor spray patterns when utilized in aerosol or pump sprays. The catalyst employed in the present invention is utilized within the range of between about 0.2 weight % and about 0.8 weight %, preferably between about 0.25 weight % and about 0.6 weight % based on total reaction mixture.

In the formation of the vinyl ester/maleic anhydride copolymer, it has been found beneficial to initiate the polymerization with a small portion of the vinyl ester and to add the major portion slowly over a period of from about 0.5 to about 3 hours to the maleic anhydride reaction mixture. Aliquot samples of the reaction mixture may be taken to determine the extent of reaction to the desired copolymer viscosity indicating molecular weight. The reaction is usually completed within a period of from about 1 to 8 hours after the final addition of the vinyl ester. The reaction is also carried out in the presence of a solvent such as for example benzene, toluene or acetone. Where benzene or toluene are employed, the reaction product, i.e. the vinyl ester/maleic anhydride copolymer is formed as a slurry and is recovered by filtration, in a dry-precipitation polymerization reaction. When acetone is the solvent employed, as in solution polymerization, the vinyl ester/maleic anhydride copolymer is obtained as a light viscous solution and can be recovered by distillation to remove solvent or the unseparated solvent solution can be used in the second esterification step.

In the second step, the preformed polymer of this first step, i.e. the alternating vinyl ester/maleic anhydride copolymer, is reacted with an aliphatic alcohol of from 1 to 6 carbon atoms in a 1:1 mole ratio of maleic anhydride to alcohol; although this ratio may be varied within the range of from about 0.25:1 to about 1:6 when esterification of all anhydride groups are not required or when an excess of alcohol in the product is useful, i.e. functioning as a solvent. For example, when the acetone solvent solution of the first step is employed, the esterification is carried out with the addition of alcohol, for example ethanol at 70–75° C. over a period of about 3 hours. Upon completion of the esterification, the acetone can be recovered by distillation and recycled. The preparation of mixed alkyl maleic ester copolymers is also included within the scope of this invention and is carried out by either simultaneous or sequential addition of alcohols to the vinyl ester/maleic anhydride copolymer. The esterification reaction is also effected under anhydrous conditions under a nitrogen atmosphere, generally at a temperature of between about 50° C. and about 155° C. for a period of from 1 to 8 hours. After completion of the second step, the reaction mixture is cooled to room temperature and the vinyl ester/maleic acid half ester recovered by filtration or by any other convenient and conventional method. It is to be understood that, although modifications of the above process in the manner of product preparation, purification and recovery can be made without departing from the scope of this invention, the conditions of catalyst and monomer concentration and reaction temperature should be strictly adhered to if random or block polymers or high molecular weight polymers are to be avoided.

Illustrative of the vinyl esters employed for the resins of the present process, there may be mentioned vinyl acetate, vinyl propionate, vinyl isopropionate, vinyl isobutyrate, vinyl butyrate and vinyl hexonate. Examples of suitable aliphatic alcohols include methanol, ethanol, propanol, isopropanol, butanol, isobutanol and the like.

The present resins are incorporated in a standard hair spray formulation in a concentration of between about 0.5% and about 20% by weight preferably between about 2% and 12% by weight. The method of incorporation involves no special technique and is achieved by merely mixing the present products in the above concentrations in an existing hair spray formulation or combining the individual ingredients of a conventional hair spray in accordance with standard methods and admixing the present product as the active hair spray agent. Generally when an aerosol spray is desired, the resin is employed between about 5 and about 25% by weight based on propellant. In the case of pump system, the resin is employed between 0.5% and about 20% by weight of total formulation.

As indicated above, the propellants for hair spray include carbon dioxide, those conventionally employed in aerosols, anhydrous alcohol/halo hydrocarbon systems, methylene chloride and alcohol-carbon dioxide or hydrocarbon propellant systems such as isobutane and propane. The use of 20/10 to 50/50 trichlorofluoromethane and dichlorodifluoromethane propellant mixtures fail to precipitate the present hair spray resins so that the need for nitrous oxide is not required. Perfumes, preservatives, surfactants and UV absorbers may also be incorporated in the formulation.

Having thus described the invention, reference is now had to the accompanying examples which are presented as preferred embodiments of the invention or as comparisons with commercial hair spray resins, but which are not to be construed as limiting to the scope of the invention as more broadly set forth above and in the appended claims. In the following example, all amounts and proportions are by weight unless otherwise indicated.

EXAMPLE 1

Preparation of 50/50 Alternating Vinyl Acetate/Ethyl Maleate Copolymer

A. Maleic anhydride (98 g), vinyl acetate (26 g) and toluene (480 ml) were charged to a 500 ml kettle, the temperature was raised to 63–65° C. and 1 gram of 2,2'-azobis (2,4-dimethyl valeronitrile) in 20 ml of toluene was added. Polymerization was started under a blanket of nitrogen, an additional 60 g of vinyl acetate was slowly added over a 60 minute period and the temperature was maintained at 65° C. for an additional 5 hours. Subsequent sampling showed residual maleic anhydride concentration less than 1%. The reaction mixture was then cooled to 40° C. and the resulting polymer slurry was transferred to a Buchner funnel from which the vinyl acetate/maleic anhydride copolymer is recovered by filtration as a white powder. The powder was twice washed with toluene to remove residual maleic anhydride and then dried at 70° C. in a vacuum oven. The yield of alternating vinyl acetate/maleic anhydride (VA/MA) copolymer was 92% based on conversion of maleic anhydride.

Into a 500 ml kettle was charged 165 g of the above VA/MA copolymer and 247.62 g of absolute ethanol. The mixture was heated to 78° C. under a blanket of nitrogen for 5 hours to yield a 50% solid solution. The reaction mixture was then cooled to 40° C. and the product, vinyl acetate/ethyl maleate (VA/EM) copolymer (49.70% solids in ethanol) was recovered and found to have a relative viscosity of 1.25, a specific viscosity of 0.25. The K value of this copolymer is 31.

B. The above example was repeated except that 426.56 g (480 ml) of benzene were used instead of 480 ml of toluene. The VA/EM product was washed with benzene instead of toluene and the vinyl acetate/maleic anhydride copolymer was obtained in 90% yield as a white powder. Esterification of 160 g of the VA/MA product with 240.12 g of absolute ethanol, as in part A, produced 49.71% VA/EM alternating copolymer in ethanol having a relative viscosity of 1.47.

C. Part A above was repeated except that 535 ml of acetone were introduced into the kettle in place of 480 ml of toluene and the vinyl acetate/maleic anhydride polymerization was carried out at 53° C. instead of 63–65° C. Esterification of the VA/MA was achieved with 262 g of absolute ethanol by conducting the reaction at 70–75° C. for about 3 hours. The acetone was distilled off and the vinyl acetate/ethyl maleate (VA/EM) alternating copolymer was recovered as a solution of 44.18% copolymer solids in ethanol having a relative viscosity of 1.26, a specific viscosity of 0.26 and a K value of 31.

EXAMPLE 2

Preparation of 50/50 Alternating Vinyl Acetate/Propyl Maleate Copolymer

To 160 g of vinyl acetate/maleic anhydride copolymer, prepared as described in Example 1A, was added 264.52 g of 1-propanol in a 500 ml kettle. This mixture was heated to 90° C. in a nitrogen atmosphere for 5 hours to effect esterification. After 5 hours, the alternating vinyl acetate/propyl maleate copolymer was obtained in a 50% solids solution. The solution was then cooled to 40° C. and product recovered. Analysis showed 46.86% solid in solution; a relative viscosity of 1.25 and a specific viscosity of 0.25, this product has a K value of 30.

EXAMPLE 3

Preparation of 50/50 Alternating Copolymer of Vinyl Acetate/Isopropyl Maleate The procedure in Example 2 was repeated except that isopropanol was substituted for 1-propanol. Results showed 43.04% vinyl acetate/isopropyl maleate alternating copolymer in isopropanol; 1.25 relative viscosity and 0.25 specific viscosity. This product has a 30K value.

EXAMPLE 4

Preparation of 50/50 Alternating Copolymer of Vinyl Acetate/n-Butyl Maleate

The procedure in Example 2 was repeated except that 288.9 g of n-butanol was substituted for 264.52 g of 1-propanol. The reaction product, vinyl acetate/n-butyl maleate alternating polymer, was obtained as 47.09% copolymer solids in solution; and had a relative viscosity of 1.24 and a specific viscosity of 0.24. This product has a K value of 30.

EXAMPLE 5

Preparation of 50/50 Alternating Vinyl Propionate/Ethyl Maleate Copolymer

A. Maleic anhydride (98 g), vinyl propionate (30 g) and toluene (5/5.25 ml) were charged to a 500 ml kettle. The temperature was raised to 63°–65° C. and 0.1 g of 2,2'-azobis(2,4-dimethyl valeronitrile) in 20 ml of toluene was added. An additional 70.12 g of vinyl propionate is slowly added over a 60 minute period and the temperature was maintained at 65° C. for an additional 5 hours under a blanket of nitrogen. Subsequent sampling showed residual maleic anhydride concentration less than 1%. The reaction mixture was then cooled to 40° C. and the resulting polymer slurry was transferred to a Buchner funnel from which the vinyl propionate/maleic anhydride (VP/MA) copolymer is recovered by filtration as a white powder. The powder was washed twice with toluene to remove residual maleic anhydride and then dried at 70° C. in a vacuum oven. The yield of alternating vinyl propionate/maleic anhydride copolymer was 92% based on conversion of maleic anhydride.

Into a 500 ml kettle was charged 160 g of the above VP/MA copolymer and 240.12 g of absolute ethanol. The mixture was heated to 75° C. under a blanket of nitrogen for 5 hours to yield a 50% solid copolymer in solution. The reaction mixture was then cooled to 40° C. and product, vinyl propionate/ethyl maleate copolymer (52.37% solids in ethanol) was recovered and found to have a relative viscosity of 1.24 and a specific viscosity of 0.24. This product has a K value of 30.

EXAMPLE 6

Preparation of 50/50 Alternating Vinyl Butyrate/Ethyl Maleate Copolymer

A. Maleic anhydride (55.86 g) vinyl butyrate (19.5 g) and toluene (308 ml) were charged to a 500 ml kettle. The temperature was raised to 63°–65° C. and 0.65 g of 2,2'-azobis(2,4-dimethyl valeronitrile) in 20 ml of toluene was added. An additional 45.5 g of vinyl butyrate is slowly added over a 60 minute period and the temperature is maintained at 65° C. for 5 hours under a blanket of nitrogen. Subsequent sampling showed residual maleic anhydride concentration less than 1%. The reaction mixture was then cooled to 40° C. and the resulting polymer slurry was transferred to a Buchner funnel from which the vinyl butyrate/maleic anhydride copolymer is recovered by filtration as a white powder. The powder was twice washed with toluene to remove residual maleic anhydride and then dried at 70° C. in a vacuum oven. The yield of alternating vinyl butyrate/maleic anhydride copolymer was 84% based on conversion of maleic anhydride.

Into a 500 ml kettle was charged 96 g of the above vinyl butyrate/maleic anhydride copolymer and 144 g of absolute ethanol. The mixture was heated to 78° C. under a blanket of nitrogen for 5 hours to yield a 50% solid solution. The reaction mixture was then cooled to 40° C. and product, vinyl butyrate/ethyl maleate copolymer (42.29% solid copolymer in ethanol) was recovered and found to have a relative viscosity of 1.24 and a specific viscosity of 0.24. This product has a K value of 30.

EXAMPLE 7 (COMPARATIVE)

As discussed above, it is essential in the preparation of the present copolymers to first copolymerize the vinyl ester with maleic anhydride under anhydrous conditions so that a charge complex is formed and will react to provide the present copolymer of critical alternating structure.

The following experiment was carried out to establish that other methods of preparation fail to provide the alternating copolymers of this invention.

To a glass reactor was added a reactant mixture of 1 mole of maleic anhydride and 1 mole ethanol in ethanol solvent (5 moles) and the mixture was stirred for 6 hours at 80° C. The maleic anhydride ring opened to form the product $C_2H_5O$—CO—CH=CH—CO—OH and no charge complex was formed. This product was recovered and 144.13 grams was contacted with 86.09 grams of vinyl acetate and stirred for 6 hours at 80° C. No copolymer was formed.

When maleic anhydride was reacted with ethanol in aqueous solution the product was a mixture of the above and HO—CO—CH=CH—CO—OH. No charge complex forms and no polymerization with vinyl acetate takes place.

EXAMPLE 8

The following is a representative formulation for an aerosol hair spray employing a typical hydrocarbon $C_3$-$C_4$ propellant.

|  | wt, (g) | % wt |
|---|---|---|
| Vinyl acetate/ethyl maleate (49.70% solids) K = 31 | 5 | 5 |
| Anhydrous ethanol | 75 | 75 |
| Propellant A-46 (Isobutane/propane 80/20) | 20 | 20 |

EXAMPLE 9

The cloud/clear temperatures, hair holding capabilities and viscosities of the present alternating vinyl ester-/alkyl maleate polymers are reported in Table I. All of the 50/50 alternating copolymers of this invention (Samples 1-10) showed good compatibility with hydrocarbon propellant mixtures, as indicated by their low clear/cloud point temperatures.

For the curl retention and clear/cloud point determinations, samples 1-10 at 50% solids concentration in solution were diluted with anhydrous ethanol to a clear solution containing 2.5% solids (resin). Samples 11-13 were copolymers of random structure, i.e. not the alternating structure of the copolymers of this invention. The difference in structure is caused by the preparation of these samples at 100° C., i.e. a temperature in excess of that at which the charge complex between the vinyl acetate and maleic anhydride exists (upper limit is about 90° C.). Except for the temperature, the general preparation of Example 1 was followed for samples 11-13. However, in the case of samples 11-13 the ratio of vinyl acetate to maleic anhydride was also adjusted as indicated in Table I. Esterification of these random copolymers followed the procedure of Example 1A and provided the corresponding random products of samples 11-13 reported in the Table.

In preparation for the curl retention and cloud/clear point temperature determinations, sample 13 was also diluted to 2.5% solids in ethanol to form the test solutions. Samples 11 and 12 were diluted as noted.

For the curl retention tests, the diluted samples were each charged to an aerosol spray can with 20% hydrocarbon propellant A-46 (blend of 20/80 propane/isobutane) and sprayed on the hair. The % curl retention values were reported after 60 minutes at 80° F. and relative humidity of 90%. The results of these tests, using GANTREZ ® ES-225* as a standard, assigned a value of 1.0, are shown in Table I.

*an alternating copolymer of methyl vinyl ether/ethyl maleate, commercial hair spray supplied by GAF Corporation The cloud/clear point temperatures were determined in a dry ice ethanol bath with the samples at the same solids concentration noted above for the curl retention tests.

TABLE I

| Sample | Copolymer | Prepared In | Solvent for Testing | Rel. Visc. (K Value) | Cloud/Clear Point °F. | Curl Retention≠ relative to GANTREZ ES-225 at K = 41 |
|---|---|---|---|---|---|---|
| 1 | vinyl acetate/ethyl maleate | toluene | ethanol | 1.26 (31) | <−20 both | 0.92 |
| 2 | vinyl acetate/ethyl maleate | acetone | ethanol | 1.26 (31) | <−20 both | 0.99 |
| 3 | vinyl acetate/propyl maleate | toluene | ethanol | 1.25 (30) | <−20 both | 0.93 |
| 4 | vinyl acetate/isopropyl maleate | toluene | ethanol | 1.26 (31) | <−20 both | 0.85 |
| 5 | vinyl acetate/butyl maleate | toluene | ethanol | 1.25 (30) | <−20 both | 1.05 |
| 6 | vinyl propionate/ethyl maleate | toluene | ethanol | 1.24 (30) | <−20 both | 0.76 |
| 7 | vinyl butyrate/ethyl maleate | toluene | ethanol | 1.24 (30) | <−20 both | 0.91 |
| 8 | vinyl acetate/ethyl maleate | benzene | ethanol | 1.50 (43) | <−20 both | 1.17 |
| 9 | vinyl acetate/ethyl maleate | toluene | ethanol | 1.20 (27) | <−20 both | 0.79 |
| 10 | vinyl acetate/ethyl maleate | methylene chloride | ethanol | 2.17 (63) | <−20 both | 2.16 (1) |
| 11 | *vinyl acetate/ethyl maleate (90/10) | toluene | ethanol | 1.24 (29) | >75 both | — |
| 12 | **vinyl acetate/ethyl maleate (60/40) | toluene | ethanol | 1.23 (29) | <−20 both | 0.67 |
| 13 | ***vinyl acetate/ethyl maleate (50/50) | toluene | ethanol | 1.17 (24) | <−20 both | 0.43 |
| 14 | methyl vinyl ether/ethyl maleate (GANTREZ ES-225) | benzene | ethanol | 1.44 (41) | 14/16 | 1.00 |

*random structure (90% vinyl acetate/10% ethyl maleate) not soluble in ethanol/propellant system.
**random structure (60% vinyl acetate/40% ethyl maleate).
***random structure (50% vinyl acetate/50% ethyl maleate)
(1) less desirable spray pattern - tendency to stream because of molecular weight
≠differences of 0.10 or greater represent significant differences in hair holding performance.

EXAMPLE 10 (COMPARATIVE)

The following samples in Table II at comparable viscosities and molecular weights were reported to show the superiority of the present vinyl ester monomer over the vinyl ether in the alternating copolymer resins. The preparation of test samples 15-20 was the same as described in Example 9.

TABLE II

| Sample | Copolymer | Solvent for Testing | Rel. Visc. (K Value) | Cloud/Clear Point °F. | Curl Retention≠ Relative to GANTREZ ES-225 at K = 41 |
|---|---|---|---|---|---|
| 15 | vinyl acetate/ethyl maleate | ethanol | 1.26 (31) | <−20 both | 0.99 |
| 16 | methyl vinyl ether/ethyl maleate | ethanol | 1.27 (31) | 10 both | 0.83 |
| 17 | vinyl acetate/ethyl maleate | ethanol | 1.43 (40) | <−20 both | 1.17 |
| 18 | methyl vinyl ether/ethyl | ethanol | 1.44 (41) | 14/16 | 1.00 |

TABLE II-continued

| Sample | Copolymer | Solvent for Testing | Rel. Visc. (K Value) | Cloud/Clear Point °F. | Curl Retention≠ Relative to GANTREZ ES-225 at K = 41 |
|---|---|---|---|---|---|
|  | maleate (GANTREZ ES-225) |  |  |  |  |
| 19 | vinyl butyrate/ethyl maleate | ethanol | 1.24 (30) | < −20 both | 0.91 |
| 20 | butyl vinyl ether/ethyl maleate | ethanol | 1.26 (31) | < −10 both | 0.31 |

≠Differences of 0.10 or greater represent significant differences in hair holding performances.

In the above Table it is noted that the vinyl butyrate-/ethyl maleate is significantly superior in high humidity holding (60 min at 80° F., 90% relative humidity) than the butyl vinyl ether/ethyl maleate. Similarly it is shown that the vinyl acetate/ethyl maleate at lower relative viscosity and K value is equivalent to the higher viscosity GANTREZ ® ES-225 and has a cloud/clear point greatly improved over GANTREZ polymer at equivalent molecular weight. This superiority of the vinyl ester/alkyl maleates over the vinyl ether/alkyl maleates provides improved handling of concentrates and superior spray patterns of the present lower molecular weight copolymers coupled with the excellent hair holding capability previously found only with higher molecular weight resins.

EXAMPLE 11 (COMPARATIVE)

The following samples compare the present hair spray resins with other commercial hair spray resins. The same testing procedures as set forth in Example 9 are repeated. The results are reported in Table III.

TABLE III

| Sample | Copolymer | Solvent for Testing | Rel. Visc. (K Value) | Cloud/Clear Point °F. | Curl Retention≠ Relative to GANTREZ ES-225 at K = 41 |
|---|---|---|---|---|---|
| 21 | vinyl acetate/ethyl maleate | ethanol | 1.26 (31) | < −20 both | 0.99 |
| 22 | vinyl pyrrolidone/ethyl maleate | ethanol | 1.26 (31) | < −20 both | 0.65 |
| 23 | vinyl pyrrolidone/vinyl acetate | ethanol | 1.26 (31) | 40/52 | 0.76 |
| 24 | N.S. Resin 28-2930* | ethanol | - - | 18/23 | 0.79 |
| 25 | ethylene/ethyl maleate** | ethanol | 1.32 (35) | < −20 both | 0.83 |
| 26 | methyl vinyl ether/ethyl maleate (GANTREZ ES-225) | ethanol | 1.44 (41) | 14/16 | 1.00 |

*random terpolymer of vinyl acetate, crotonic acid and vinyl neodecanate, supplied by National Starch & Chemical Corp.
**supplied by Monsanto
≠Difference of 0.10 or greater represent significant differences in hair holding performance.

The above data shows that when vinyl pyrrolidone (a well known monomer used in hair sprays) is substituted for either the ethyl maleate or vinyl acetate of the present resins, the curl holding at high humidity falls off to the extent that the resulting polymer is ineffective in the hair spray. The National Starch resin has acceptable hair holding properties but the relatively high cloud/clear point temperature indicates that it is not sufficiently stable in aerosol formulations or compatible with hydrocarbons conventionally used as propellant.

EXAMPLE 12 (COMPARATIVE)

The following formulations of vinyl acetate/ethyl maleate, (40.66% solids) of Sample 1 and GANTREZ ES-225 were prepared for comparison of shelf stability, noncorrosivity and other properties reported in the following Table IV.

Formulation I and II concentrates were introduced into an epoxy coated spray can. A valve top was then attached and sealed onto each container and propellant was charged through the valve so that each container contained 150 g of formulation, of which 2.5% represented resin solids under about 36 psig.

The sealed containers were then placed in a 45° C. oven where they were held for 3 months. The above tests were carried out in duplicate. The results are reported in the following Table IV.

TABLE IV

Shelf Stability and Corrosion Studies

|  | Formulation I (wt %) | Formulation II (wt %) |
|---|---|---|
| Vinyl acetate/ethyl maleate | 6.15 | — |
| GANTREZ ES-225 | — | 5.00 |
| Amino methyl propanol (neutralizer) | — | 0.11 |
| Anhydrous ethanol | 68.85 | 69.89 |
| Propellant A-46 | 25.00 | 25.00 |
| Initial pH of the copolymer | 3.1 | 6.5 |
| Final pH of formulation after 3 mo. on releasing spray from container | 3.4 | 5.5 |
| Odor-degradation of formulation or container lining | none | none |
| Appearance concentrate | Hazy white | Cloudy yellow (slight pptn.) |
| Container degradation-corrosion | none | none |
| Pressure, at 70° F. | no loss | no loss |

In the above Table, the pH of the present copolymer showed no substantial change (0.3) which indicates higher stability than the GANTREZ copolymer. The pressure in the container at 70° F. was measured to determine any container rupture due to corrosion or formulation degradation. No rupture occurred in either case. Resistance to corrosion is noted for all of the resins of this invention, notwithstanding the fact that they are employed in a non-neutralized, acidic condition.

What is claimed is:

1. In a hair spray formulation containing a hair spray resin, the improvement which comprises using essentially the polymer having the formula

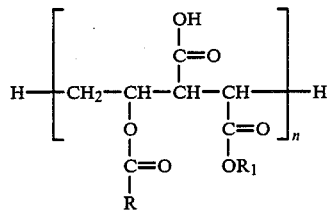

as the hair spray resin wherein R and $R_1$ are each independently alkyl having from 1 to 6 carbon atoms and n has a value of between about 40 and about 250, which resin has a relative viscosity of between about 1.12 and about 2.03 and is derived from a preformed vinyl ester-maleic anhydride alternating copolymer.

2. The hair spray of claim 1 wherein the resin is the alternating vinyl acetate-ethyl maleate copolymer.

3. The hair spray of claim 1 wherein the resin, R is alkyl having from 1 to 3 carbon atoms and $R_1$ is alkyl having from 2 to 4 carbon atoms.

4. The hair spray of claim 1 wherein the resin, R is methyl, $R_1$ is ethyl and n has a value of from about 60 to about 220.

5. The hair spray of claim 1 wherein the resin, each of R or $R_1$ is a mixture of alkyl groups.

6. A hair spray formulation comprising an effective hair holding amount of the resin of claim 1 and an inert carrier therefor.

7. The hair spray resin of claim 1 prepared as a concentrate of 50 weight % resin in an inert carrier.

8. The hair spray of claim 1 wherein the resin, R is methyl and $R_1$ is alkyl having 1 to 6 carbon atoms.

9. A hair spray formulation containing between about 0.5 and about 20% by weight of the copolymer of claim 1, wherein said copolymer is present in an amount of from about 5% to about 25% by weight with respect to any propellant in the formulation.

* * * * *